(12) United States Patent
Koh

(10) Patent No.: US 7,676,260 B1
(45) Date of Patent: Mar. 9, 2010

(54) IMPLANTABLE CARDIAC STIMULATION DEVICE THAT MONITORS PROGRESSION AND REGRESSION OF HEART DISEASE RESPONSIVE TO DIFFERENCES IN AVERAGED ELECTROGRAMS AND METHOD

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 452 days.

(21) Appl. No.: 11/740,733

(22) Filed: Apr. 26, 2007

(51) Int. Cl.
*A61B 5/04* (2006.01)
(52) U.S. Cl. ........................... 600/509; 600/508
(58) Field of Classification Search .............. 600/508, 600/509
See application file for complete search history.

(56) References Cited

U.S. PATENT DOCUMENTS

| | | | |
|---|---|---|---|
| 5,466,254 A | 11/1995 | Helland | |
| 6,731,985 B2 * | 5/2004 | Bradley et al. | 607/28 |
| 6,748,261 B1 | 6/2004 | Kroll et al. | |
| 7,272,443 B2 | 9/2007 | Min et al. | |
| 2005/0033368 A1 | 2/2005 | Fishler et al. | |
| 2005/0216067 A1 | 9/2005 | Min et al. | |
| 2007/0288059 A1 | 12/2007 | Davenport et al. | |

FOREIGN PATENT DOCUMENTS

| | | |
|---|---|---|
| EP | 1118307 A1 | 7/2001 |
| EP | 1582233 A2 | 10/2005 |
| EP | 1582233 A3 | 6/2006 |
| EP | 1118307 B1 | 10/2007 |

OTHER PUBLICATIONS

Ebner, Erich et al., "Ventricular Evoked Response as Clinical Marker for Hemodynamic Changes in Dilative Cardiomyopathy," PACE. 2004;27:166-174.

* cited by examiner

*Primary Examiner*—Carl H Layno
*Assistant Examiner*—Yun Haeng Lee

(57) ABSTRACT

An implantable cardiac stimulation device monitors the progression and/or regression of heart disease. The device comprises a sensing circuit that senses activity of a heart and provides an electrogram for each one of a plurality of cardiac cycles, an averaging circuit that averages a number of the plurality of electrograms at spaced apart intervals to provide averaged trend electrograms, and a data generator that provides a metric reflective of progression or regression of heart failure responsive to a difference between a current averaged trend electrogram and a previous averaged trend electrogram.

19 Claims, 4 Drawing Sheets

IMPLANTABLE CARDIAC STIMULATION DEVICE THAT MONITORS PROGRESSION AND REGRESSION OF HEART DISEASE RESPONSIVE TO DIFFERENCES IN AVERAGED ELECTROGRAMS AND METHOD

FIELD OF THE INVENTION

The present invention generally relates to an implantable cardiac stimulation device. The present invention more particularly relates to such a device that monitors progression and/or regression of heart disease by morphological differences in averaged electrograms (EGM's).

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered to be comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing and/or sensing electrode configurations. In the unipolar configuration, the pacing stimulation pulses are applied or intrinsic responses are sensed between a single electrode carried by the lead, in electrical contact with the desired heart chamber, and the pulse generator case. The electrode serves as the cathode (negative pole) and the case serves as the anode (positive pole). In the bipolar configuration, the pacing stimulation pulses are applied or intrinsic responses are sensed between a pair of closely spaced electrodes carried by the lead, in electrical contact with the desired heart chamber, with the most proximal electrode serving as the anode and the most distal electrode serving as the cathode.

Pacemakers deliver pacing pulses to the heart to induce a depolarization and a mechanical contraction of that chamber when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses in one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

Recently, there has been the introduction of pacing systems that stimulate in corresponding chambers of the heart as, for example, the right ventricle (RV) and left ventricle (LV). These are termed biventricular stimulation devices.

Biventricular pacing has been shown to coordinate contractions of the left and right ventricles, reduce the amount of blood flow that leaks through the mitral valve, and decreases the motion of the septal wall that separates the chambers of the heart. Such motion can affect the quantity of blood that the ventricle can pump out in a single beat.

Biventricular pacing has been found to be particularly advantageous in patient's suffering from congestive heart failure (CHF) because of the improved ability of the left ventricle to fully pump blood from the heart. As a result, patients are able to tolerate greater exertion, have a longer life span, and experience a higher quality of life.

Congestive heart failure (CHF) is a debilitating, end-stage disease in which abnormal function of the heart leads to inadequate blood flow to fulfill the needs of the body's tissues. Typically, the heart loses propulsive power because the cardiac muscle loses capacity to stretch and contract. Often, the ventricles do not adequately fill with blood between heartbeats and the valves regulating blood flow may become leaky, allowing regurgitation or backflow of blood. The impairment of arterial circulation deprives vital organs of oxygen and nutrients. Fatigue, weakness, and inability to carry out daily tasks may result.

Not all CHF patients suffer debilitating symptoms immediately. Some may live actively for years. Yet, with few exceptions, the disease is relentlessly progressive.

As CHF progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output.

Current standard treatment for heart failure is typically centered around medical treatment using ACE inhibitors, diuretics, and digitalis. It has also been demonstrated that aerobic exercise may improve exercise tolerance, improve quality of life, and decrease symptoms. Only an option in 1 out of 200 cases, heart transplantation is also available. Other cardiac surgery is also indicated for only a small percentage of patients with particular etiologies. Although advances in pharmacological therapy have significantly improved the survival rate and quality of life of patients, patients who are refractory to drug therapy, have a poor prognosis and limited exercise tolerance.

Cardiac pacing is now considered a primary treatment for patients with drug-refractory CHF. By tracking the progression or regression of the heart disease more closely, stimulation therapy could be managed more effectively. Hence, it would be advantageous if the implanted cardiac stimulation device were able to aid in the tracking of the progression or regression of the heart disease.

One method of tracking a patient's CHF condition relies upon electrogram (EGM) morphology. Unfortunately, this has required the implanted device to locally store one averaged EGM periodically and then turn computations based on the averaged EGM's over to an external programmer. This not only requires excessive memory space within the device, but also time and device battery energy loss to support the data transfer from the device to the programmer. Hence, it would be desirable if the implantable device could monitor the progression and/or regression of heart disease without requiring excessive memory space or consuming excessive time and battery power. The present invention addresses these and other issues.

SUMMARY

There is described an implantable cardiac stimulation device comprising a sensing circuit that senses activity of a heart and provides an electrogram for each one of a plurality of cardiac cycles, an averaging circuit that averages a number of the plurality of electrograms at spaced apart intervals to provide averaged trend electrograms, and a data generator that provides a metric reflective of progression or regression of heart failure responsive to a difference between a current averaged trend electrogram and a previous averaged trend electrogram.

The device may further comprise a pulse generator that provides pacing pulses to the heart. The averaged trend electrograms may be averaged paced evoked response electrograms and the metric may be a difference in pacing depolarization integral. The metric may in addition or alternatively be a difference in the peak to peak swings between the current averaged trend electrogram and the previous averaged trend electrogram. Still further, the metric may in addition or alternatively be a difference in the maximum slope between the current averaged trend electrogram and the previous averaged trend electrogram. Still further, the metric may in addition or alternatively be a difference in an electrogram zero crossing point between the current averaged trend electrogram and the previous averaged trend electrogram.

The spaced apart intervals are preferably periodic intervals. The periodic intervals may be, for example, on the order of daily intervals.

The device may further comprise a pulse generator that provides pacing pulses to the heart, and the averaging circuit then averages paced depolarization electrograms.

The averaging circuit preferably averages consecutive paced depolarization electrograms. The averaging circuit may average on the order of ten consecutive paced depolarization electrograms to provide each averaged trend electrogram and remove the patient's respiration cycle.

The device may further comprise a morphology circuit that aligns the number of electrograms before the averaging circuit averages the number of electrograms. The morphology circuit preferably aligns the number of electrograms with respect to delivered pacing pulses. The pacing pulses may be atrial pacing pulses ventricular pacing pulses.

According to another embodiment, an implantable cardiac stimulation device comprises a pulse generator that delivers pacing pulses to a heart, a sensing circuit that senses activity of a heart and provides an electrogram for each one of a plurality of paced cardiac cycles, an averaging circuit that averages a number of the plurality of electrograms at daily intervals to provide daily averaged trend electrograms, and a data generator that provides a metric reflective of progression or regression of heart failure responsive to a difference between a current averaged trend electrogram and an averaged trend electrogram from am immediately previous day.

In another embodiment, a method for use in an implantable cardiac stimulation device comprises sensing activity of a heart to provide an electrogram for each one of a plurality of cardiac cycles, averaging a number of the plurality of electrograms at spaced apart intervals to provide averaged trend electrograms, and generating a metric reflective of progression or regression of heart failure responsive to a difference between a current averaged trend electrogram and a previous averaged trend electrogram.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
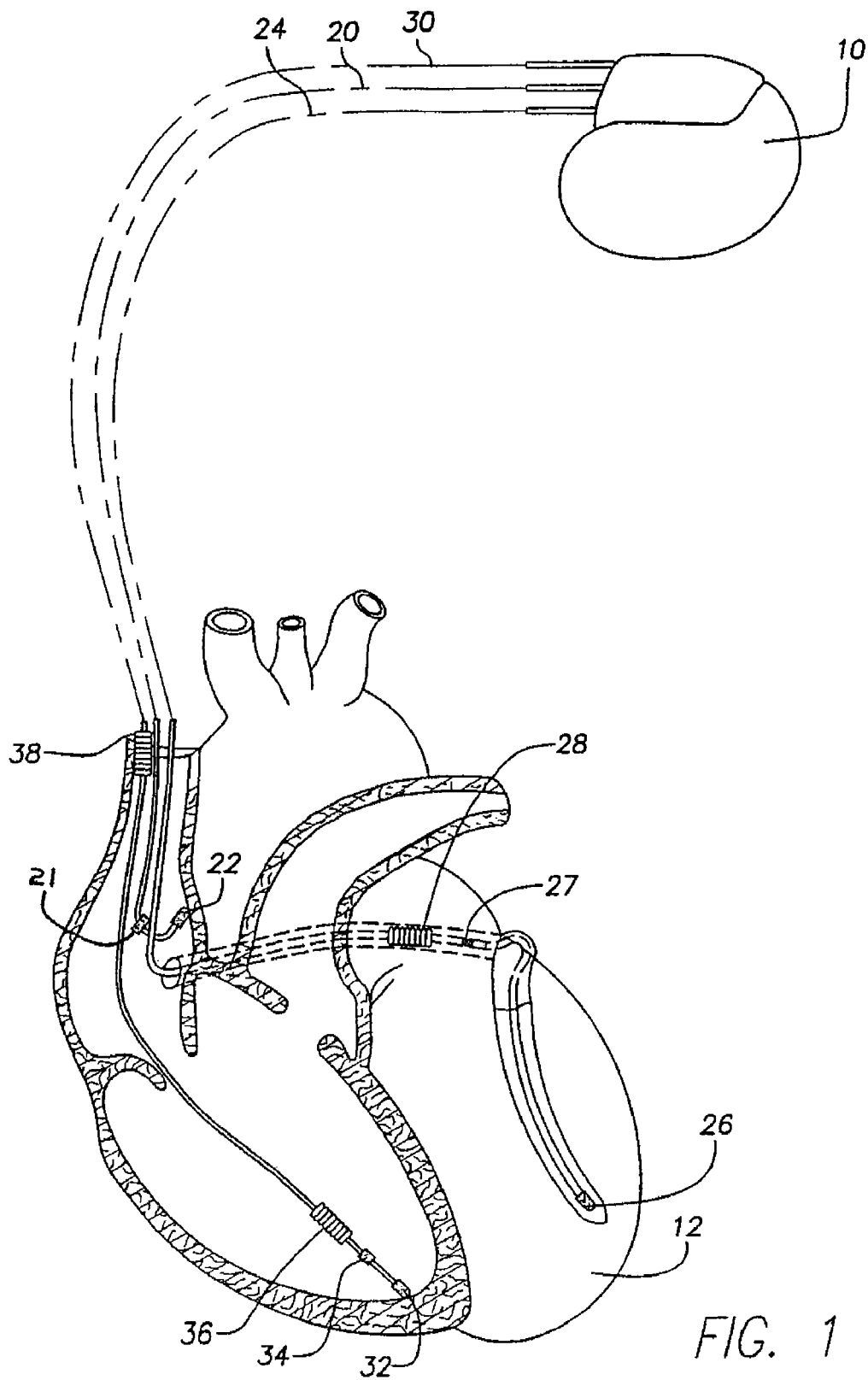
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, filed Dec. 8, 1999, entitled "A Self-Anchoring, Steerable Coronary Sinus Lead" (Pianca et. al); and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
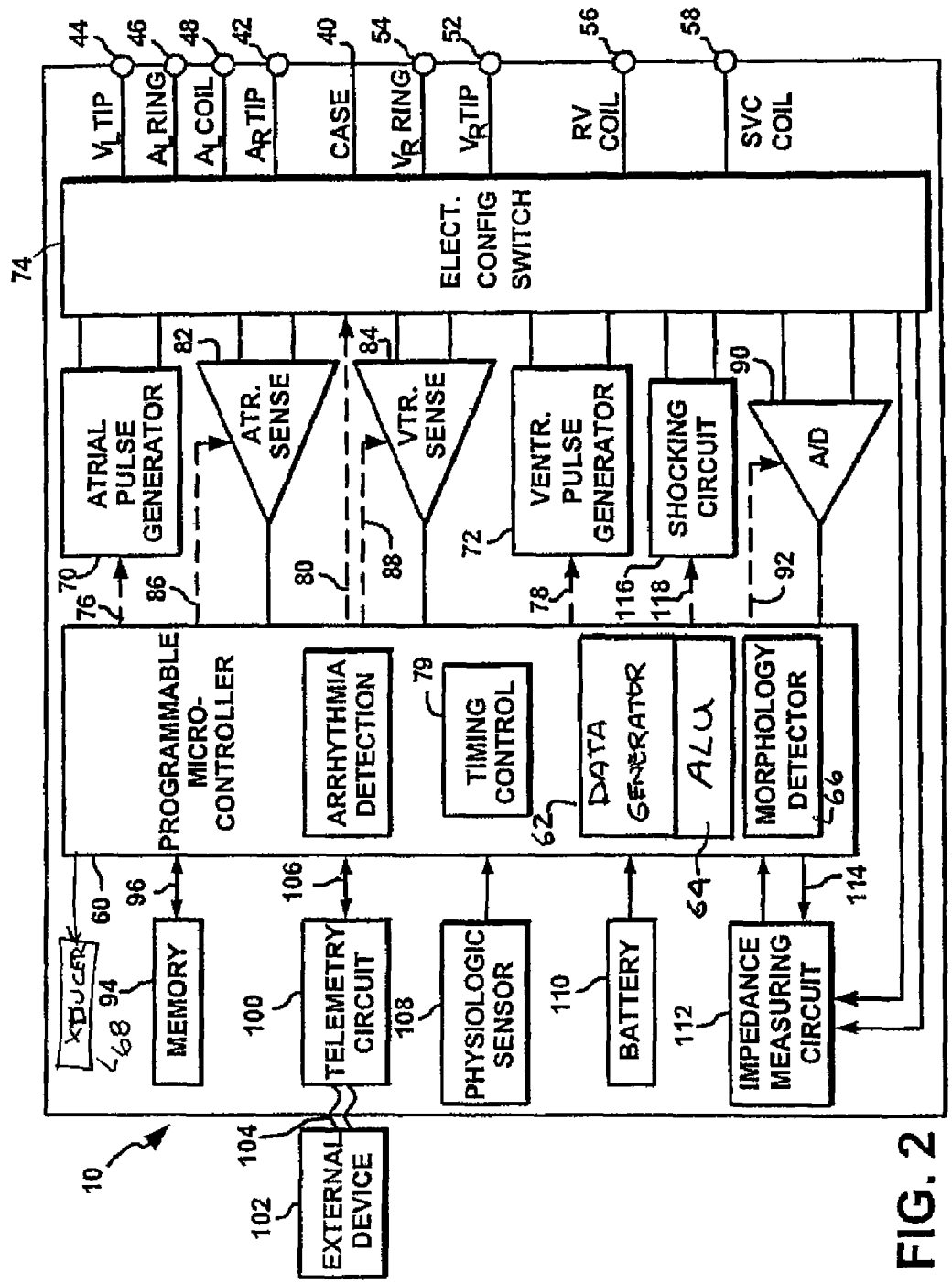
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. As will also be seen subsequently, the timing control circuitry may be used to time spaced apart intervals to initiate the storing and averaging of electrograms in accordance with one embodiment of the invention.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fibwaves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as known in the art.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

According to this embodiment, the device 10 is capable of monitoring the progression and/or regression of heart disease by generating an average trend EGM at spaced time intervals as, for example, once each day, and generating a metric related to a difference between the average trend EGM of today and a prior average trend EGM as, for example, the average trend EGM of yesterday. Hence, only the difference metrics and one average trend EGM need be stored in the device memory 94 to enable the monitoring. The average EGM difference metrics may be, for example, the difference in paced depolarization integral (PDI) of the average EGM's, a difference in peak-to-peak swing of the average EGM's, a difference in maximum slope between the average EGM's, or a difference in the electrogram zero crossing (delay) of the average EGM's.

To these ends, the device 10 further includes a data generator 62 that provides the average EGM metrics, an arithmetic logic unit (ALU) 64 of the type known in the art for calculating the EGM averages and the average EGM metrics under control of the data generator 62, and a morphology detector 66 that aligns the EGM's to be averaged before averaging. Hence, when atrial EGM's are averaged, the sense amplifier 82 may be employed for sensing atrial EGM's and when ventricular EGM's are to be averaged, the sense amplifier 84 may be employed for sensing ventricular EGM's. As previously mentioned, one average EGM may be provided each day. For each average, a plurality of consecutive paced EGM's are sensed and stored. For example, the EGM's of ten consecutive paced cardiac cycles may be collected and averaged. The number of EGM's used for averaging may, of course, vary. However, the number of EGM's used is preferably selected so that the patient's respiration cycle will be removed by the EGM averaging process. To assure paced EGM's, the pacing rate may be increased slightly to assure consecutive paced cardiac cycles.

Once the EGM's are collected, the morphology detector aligns them. The morphology detector may align the EGM's with respective to the time of delivery of the pacing pulses whether atrial or ventricle. When the ALU has calculated the new average EGM, the difference metrics may then be calculated. If the metric is the difference in PDI, the PDI of both of the average EGM's is calculated. The PDI of the prior EGM may be stored in memory 94 for present use. The PDI of the prior average EGM is then subtracted from the PDI of the current average EGM. If the difference is positive and greater than a threshold, the patient may considered to be improving. However, if the difference is more negative than a preset amount, the patient's heart disease may be considered to be worsening. The difference may then be stored for future reference. However, if a negative difference is too great, the device may provide a warning to the patient. For example, the device may include a transducer 68 that may be made to vibrate to provide a perceptible warning to the patient.

The other metrics may be similarly generated. The peak-to-peak EGM swings may be readily calculated from the average EGM's and subtracted (the prior from the current). The maximum EGM slopes may also be readily calculated by the ALU 64 from the average EGM's and subtracted (the prior from the current). The EGM zero crossings (the delay from the pacing pulse to the zero crossing) still also may be readily calculated by the ALU 64 from the average EGM's and subtracted (the prior from the current). Any one of the forgoing may indicate a progression or regression in the heart disease. For example, any one or all of a decrease in peak-to-peak EGM swing, a decrease in EGM maximum slope, and a lengthening of the zero crossing from the pacing pulse may indicate a worsening in the heart disease. The converse of any one or all may indicate the opposite conclusion.

Figure 3:
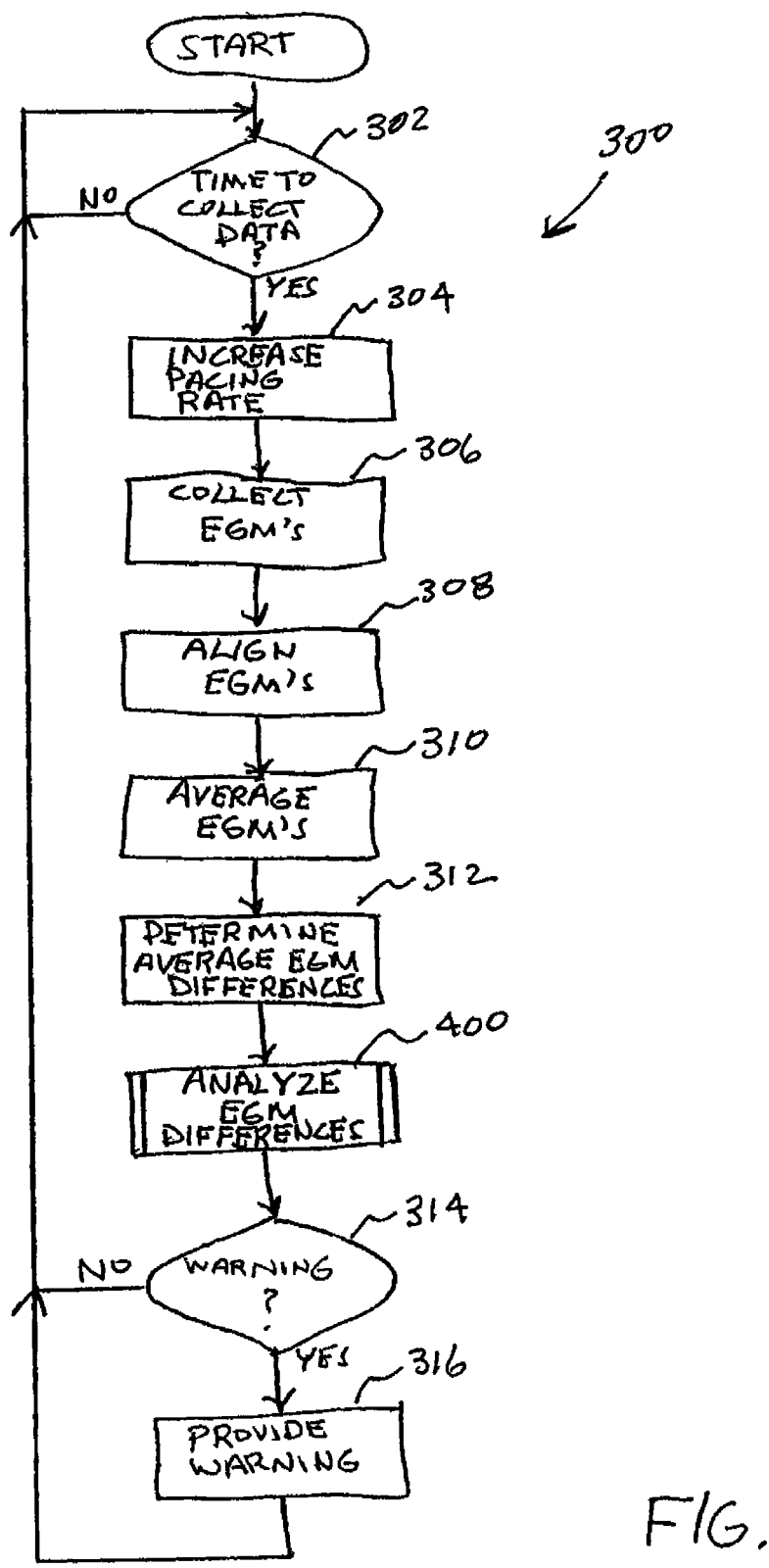
FIG. 3 is a flow chart describing an overview of the operation of one embodiment of the present invention.

In FIG. 3, a flow chart is shown describing an overview of the operation and novel features implemented in one embodiment of the device 10. In this flow chart, and the other flow chart of FIG. 4 described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of the flow chart 300 of FIG. 3 initiates with decision block 302. Here it is decided if it is time to store and average a new set of EGM's. As previously mentioned, this may be done at daily intervals, for example. If it is not time to collect, store, and average a new set of EGM's, the process returns. However, if it is time for such action, the process proceeds to activity block 304. In implementing decision block 302, another condition for advancing to activity block 304 preferably is to make sure that the patient is currently at rest. This may be accomplished by accessing the activity sensor 108. In activity block 304, the pacing rate is increased slightly, by, for example, fifteen cycles per second, to assure that the next consecutive predetermined number of cardiac cycles will be paced cardiac cycles. Once the pacing rate is increased, the process proceeds to activity block 306 where the paced evoked response EGM's of the predetermined number of consecutive cardiac cycles are collected and temporarily stored in memory 94. On the order of at least ten consecutive paced cardiac cycles would be sufficient in accordance with this embodiment. After the EGM's are collected and stored, the process advances to activity block 308 wherein the morphology detector aligns the collected EGM's with respect to the pacing pulses. The EGM's are then averaged in activity block 310.

When a current EMG average is provided by implementing activity block 310, the EGM difference metrics may be generated in accordance with activity block 312 from the current average EGM and a previous average EGM, as, for example, the average EGM of yesterday. The average EGM difference metrics may be, for example, the difference in paced depolarization integral (PDI) of the average EGM's, a difference in peak-to-peak swing of the average EGM's, a difference in maximum slope between the average EGM's, or a difference in the electrogram zero crossing (delay) of the average EGM's. According to this embodiment, the PDI difference and delay difference will be employed to monitor the progression or regression of heart disease.

The EGM difference metrics may now be analyzed in accordance with the sub-routine 400, to be described subsequently. After the analysis, it is decided in decision block 314 if a warning to the patient is required. If no warning is required, the process returns. If a warning to the patient is required, the process advances to activity block 316 where the warning is issued. The warning may be used to indicate to the patient of the need to contact the patient's physician. Once the warning is issued, the process returns. As will be seen subsequently, included within the analysis sub-routine 400 is the issuance of a report with respect to patient improvement or worsening which report may be stored in memory 94 for transmission to an external receiver 102, such as a programmer, by telemetry circuit 100.

Figure 4:
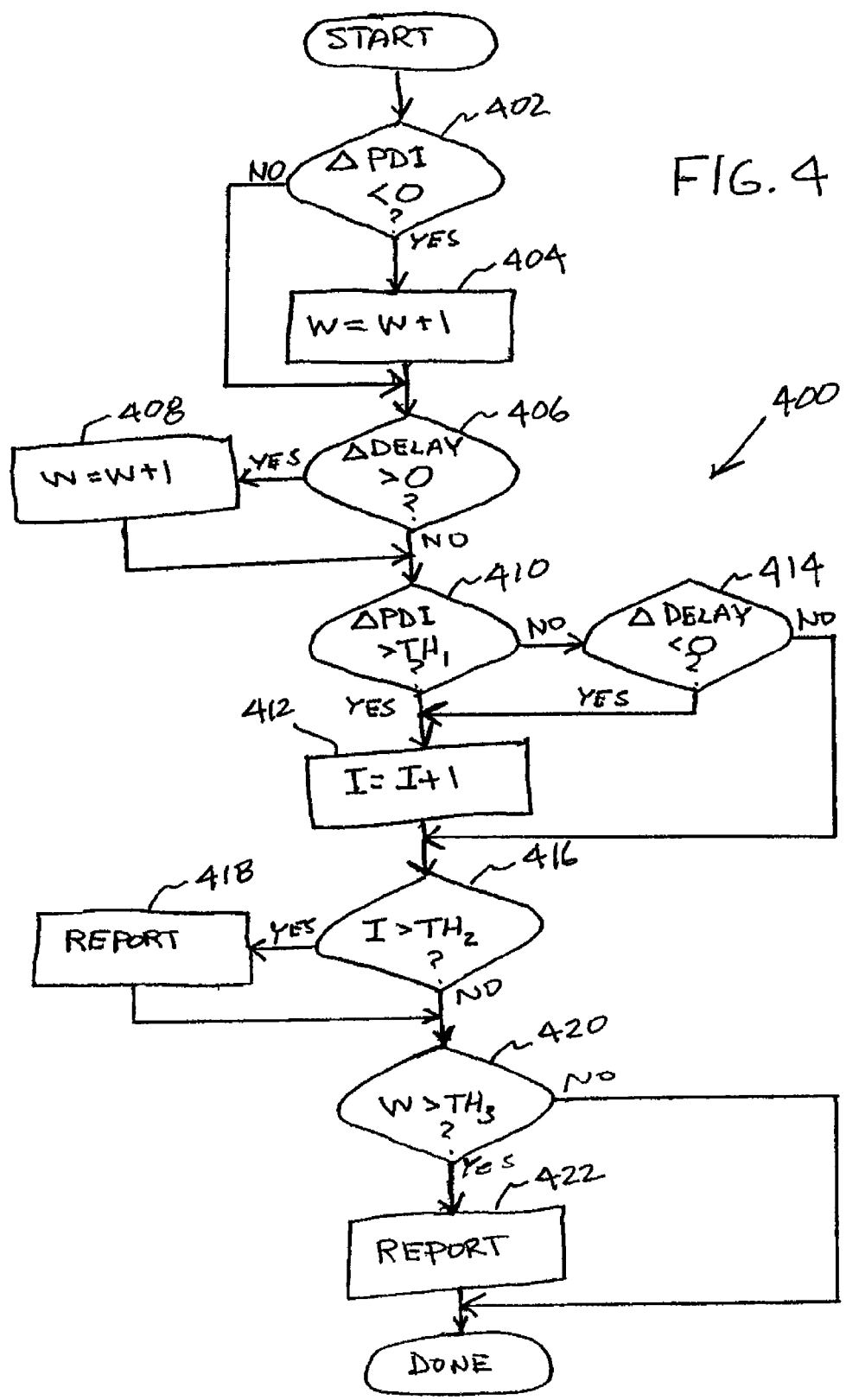
FIG. 4 is a flow chart describing an embodiment of the invention for analyzing average EGM differences in monitoring progression and/or regression of heart disease.

FIG. 4 illustrates the sub-routine 400 of FIG. 3 for analyzing the EGM difference metrics. The sub-routine 400 initiates with decision block 402 wherein it is first decided if the difference in PDI is less than zero. If it is, this indicates that the PDI of the previous average EGM is greater than the PDI of the current average EGM and that the patient's heart disease has worsened. Hence, the process then advances to activity block 404 where a worsening counter is incremented. If however, the difference in PDI is not less than zero, the process then does not increment the worsening counter but instead proceeds directly to decision block 406.

In decision block 406 it is determined if the difference in delay is greater then zero. If it is, meaning that the previous average EGM has a shorter delay time from the pacing pulse to the EGM zero crossing than the delay time from the pacing pulse to the EGM zero crossing of the current average EGM and a worsening of the patient, the process proceeds to activity block 408 wherein the worsening counter is incremented. However, if the difference in delay is not greater than zero, the process then does not increment the worsening counter but instead proceeds directly to decision block 410.

In decision block 410 it is determined if the difference in PDI is greater than a first threshold TH1. If it is, indicating an improvement in the patient's heart disease, the process advances to activity block 412 wherein an improvement counter is incremented. If however it is determined that the difference in PDI is not greater than the first threshold TH1, the process proceeds to decision block 414 wherein it is determined if the delay difference is less than zero. If the delay difference is less than zero, indicating an improvement in the patient's heart disease, the process advances to activity block 412 for incrementing the improvement counter. If the delay difference is not less than zero, indicating no improvement in the patient's heart disease or after incrementing the improvement counter in accordance with activity block 412, the process advances to decision block 416. Here it is determined if the improvement counter count is greater than a second threshold TH2 indicating sufficient improvement in the patient's heart disease to warrant the storing of a report to that effect in memory 94 for later transmission to the external device 102 by the telemetry circuit 100. If there is a sufficient count, the improvement report is provided in accordance with activity block 418. The process then completes.

If the improvement report cannot be sent then the process advances to decision block 420. Here it is determined if the worsening counter count is greater than a third threshold TH3. If it is, indicating sufficient worsening in the patient's heart disease to warrant the storing of a report to that effect in memory 94 for later transmission to the external device 102 by the telemetry circuit 100, the process advances to activity block 422 to provide the worsening report. The process then completes.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device comprising:
a sensing circuit that senses activity of a heart and provides an electrogram for each one of a plurality of cardiac cycles;
an averaging circuit that averages a number of the plurality of electrograms at spaced apart intervals to provide averaged trend electrograms; and
a data generator that provides a metric reflective of progression or regression of heart failure responsive to a difference between a current averaged trend electrogram and a previous averaged trend electrogram, wherein the metric is a difference in pacing depolarization integral.

2. The device of claim 1, further comprising a pulse generator that provides pacing pulses to the heart.

3. The device of claim 1, further comprising a pulse generator that provides pacing pulses to the heart, wherein the metric is a difference in the peak to peak swings between the current averaged trend electrogram and the previous averaged trend electrogram, and wherein the averaged trend electrograms are averaged paced evoked response electrograms.

4. The device of claim 1, further comprising a pulse generator that provides pacing pulses to the heart, wherein the metric is a difference in the maximum slope between the current averaged trend electrogram and the previous averaged trend electrogram, and wherein the averaged trend electrograms are averaged paced evoked response electrograms.

5. The device of claim 1, further comprising a pulse generator that provides pacing pulses to the heart, wherein the metric is a difference in an electrogram zero crossing point between the current averaged trend electrogram and the previous averaged trend electrogram, and wherein the averaged trend electrograms are averaged paced evoked response electrograms.

6. The device of claim 1, wherein the spaced apart intervals are periodic intervals.

7. The device of claim 6, wherein the periodic intervals are about daily intervals.

8. The device of claim 1, further comprising a pulse generator that provides pacing pulses to the heart, and wherein the averaging circuit averages paced evoked response electrograms.

9. The device of claim 1, further comprising a pulse generator that provides pacing pulses to the heart, and wherein the averaging circuit averages consecutive paced evoked response electrograms.

10. The device of claim 1, further comprising a pulse generator that provides pacing pulses to the heart, and wherein the averaging circuit averages on the order of ten consecutive paced evoked response electrograms to provide each averaged trend electrogram.

11. The device of claim 1, further comprising a morphology circuit that aligns the number of electrograms before the averaging circuit averages the number of electrograms.

12. An implantable cardiac stimulation device comprising:
a pulse generator that delivers pacing pulses to a heart;
a sensing circuit that senses activity of a heart and provides an electrogram for each one of a plurality of paced cardiac cycles;
an averaging circuit that averages a number of the plurality of electrograms at daily intervals to provide daily averaged trend electrograms; and
a data generator that provides a metric reflective of progression or regression of heart failure responsive to a difference between a current averaged trend electrogram and an averaged trend electrogram from an immediately previous day, wherein the metric is a difference in pacing depolarization integral.

13. The device of claim 12, wherein the metric is a difference in the peak to peak swings between the current averaged trend electrogram and the previous averaged trend electrogram.

14. The device of claim 12, wherein the metric is a difference in the maximum slope between the current averaged trend electrogram and the previous averaged trend electrogram.

15. The device of claim 12, wherein the metric is a difference in an electrogram zero crossing point between the current averaged trend electrogram and the previous averaged trend electrogram.

16. The device of claim 12, wherein the averaging circuit averages electrograms of consecutive cardiac cycles.

17. The device of claim 12, further comprising a morphology circuit that aligns the number of electrograms before the averaging circuit averages the number of electrograms.

18. In an implantable cardiac stimulation device, a method comprising:
sensing activity of a heart to provide an electrogram for each one of a plurality of cardiac cycles;
averaging a number of the plurality of electrograms at spaced apart intervals to provide averaged trend electrograms; and
generating a metric reflective of progression or regression of heart failure responsive to a difference between a current averaged trend electrogram and a previous averaged trend electrogram, wherein the metric is a difference in pacing depolarization integral.

19. The method of claim 18, further comprising the step of delivering pacing pulses to the heart.

* * * * *